United States Patent [19]
Wunderlich et al.

[11] Patent Number: 5,560,924
[45] Date of Patent: Oct. 1, 1996

[54] MEDICAMENT CONTAINING A 2-ARYLPROPIONIC ACID DERIVATIVE IN NANOSOL FORM AND ITS PREPARATION

[75] Inventors: Jens-Christian Wunderlich, Heidelberg; Ursula Schick, Schriesheim; Jürgen Werry, Ludwigshafen; Jürgen Freidenreich, Schriesheim; Helmut Lukas, Neu-Isenburg; Otto Schuster, Bad Soden, all of Germany

[73] Assignees: Alfatec-Pharma GmbH, Heidelberg; PAZ Arzneimittelentwicklungsgesellschaft mbH, Frankfurt am Main, both of Germany

[21] Appl. No.: 244,688

[22] PCT Filed: Dec. 4, 1992

[86] PCT No.: PCT/DE92/01012

§ 371 Date: Sep. 29, 1994

§ 102(e) Date: Sep. 29, 1994

[87] PCT Pub. No.: WO93/10761

PCT Pub. Date: Jun. 10, 1993

[51] Int. Cl.$^6$ ...................................................... A61K 9/48
[52] U.S. Cl. ......................... 424/451; 424/455; 424/456; 424/458; 424/462; 514/513; 514/568
[58] Field of Search .................................... 424/451, 455, 424/456, 458, 462; 514/513, 568

[56] References Cited

U.S. PATENT DOCUMENTS 4,880,634  11/1989  Speiser ..................... 424/450
5,430,021  7/1995   Rudnic et al. ............. 514/14

Primary Examiner—Samuel A. Acquah
Attorney, Agent, or Firm—Burns, Doane, Swecker & Mathis, LLP

[57] ABSTRACT

Immediate-effect medicaments containing a pharmacologically active 2-arylpropionic acid derivate as a pharmaceutically applicable nanosol have a considerably improved action start and bioavailability of the active substance. The 2-arylpropionic acid derivates, for example ibuprofen, flurbiprofen and ketoprofen, that are scarcely soluble in an aqueous medium, are present in a gelatine-stabilized nanosol in a form that allows these active substances to be quickly and completely resorbed already in the stomach. The disclosed colloidal disperse system composed of a 2-arylpropionic acid derivate is prepared by selecting a gelatine or gelatine derivate according to their isoelectric point (IEP), so that their IEP is adapted to the charge of the 2-arylpropionic acid derivate particles, leading to a neutral charge when the gelatine or its derivate is combined with the undissolved 2-arylpropionic acid derivate at a determined pH value. The gelatine or its derivate are converted into an aqueous sol form, their pH value is set according to the IEP of the gelatine at a value that stabilizes the nanoparticles of 2-arylpropionic acid derivate at an approximately or totally neutral charge. Before or after said last step, the 2-arylpropionic acid derivate is dissolved in the aqueous gelatine sol or a solution of 2-arylpropionic acid derivate is blended with the aqueous gelatine sol.

26 Claims, 2 Drawing Sheets

Charge distribution in Type A (acid) and Type B (alkaline) gelatins
IEP = isoelectric point

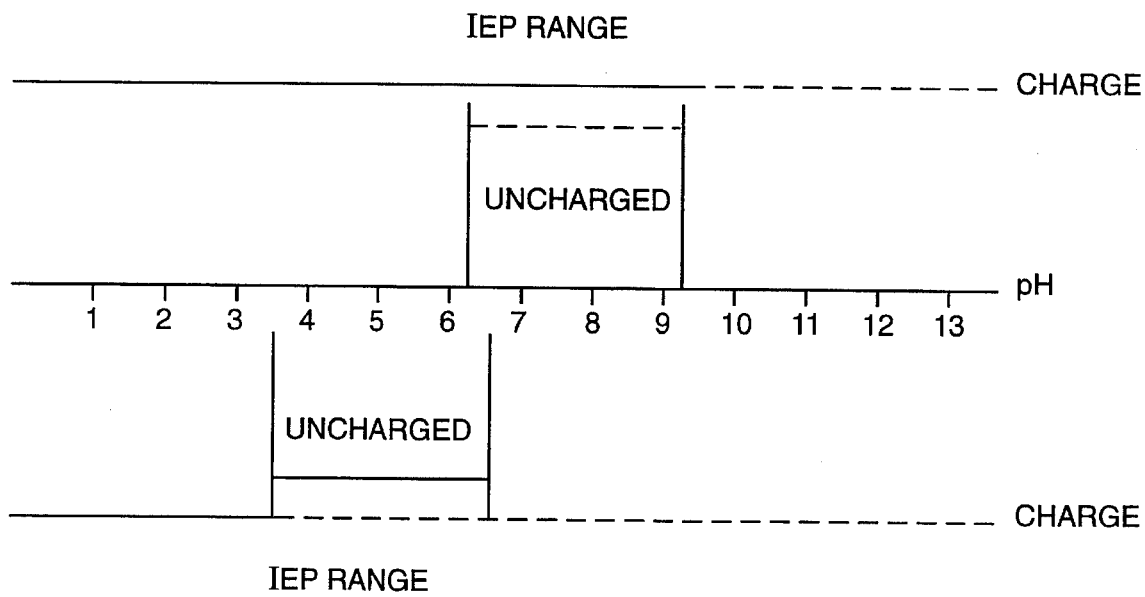
FIG._1

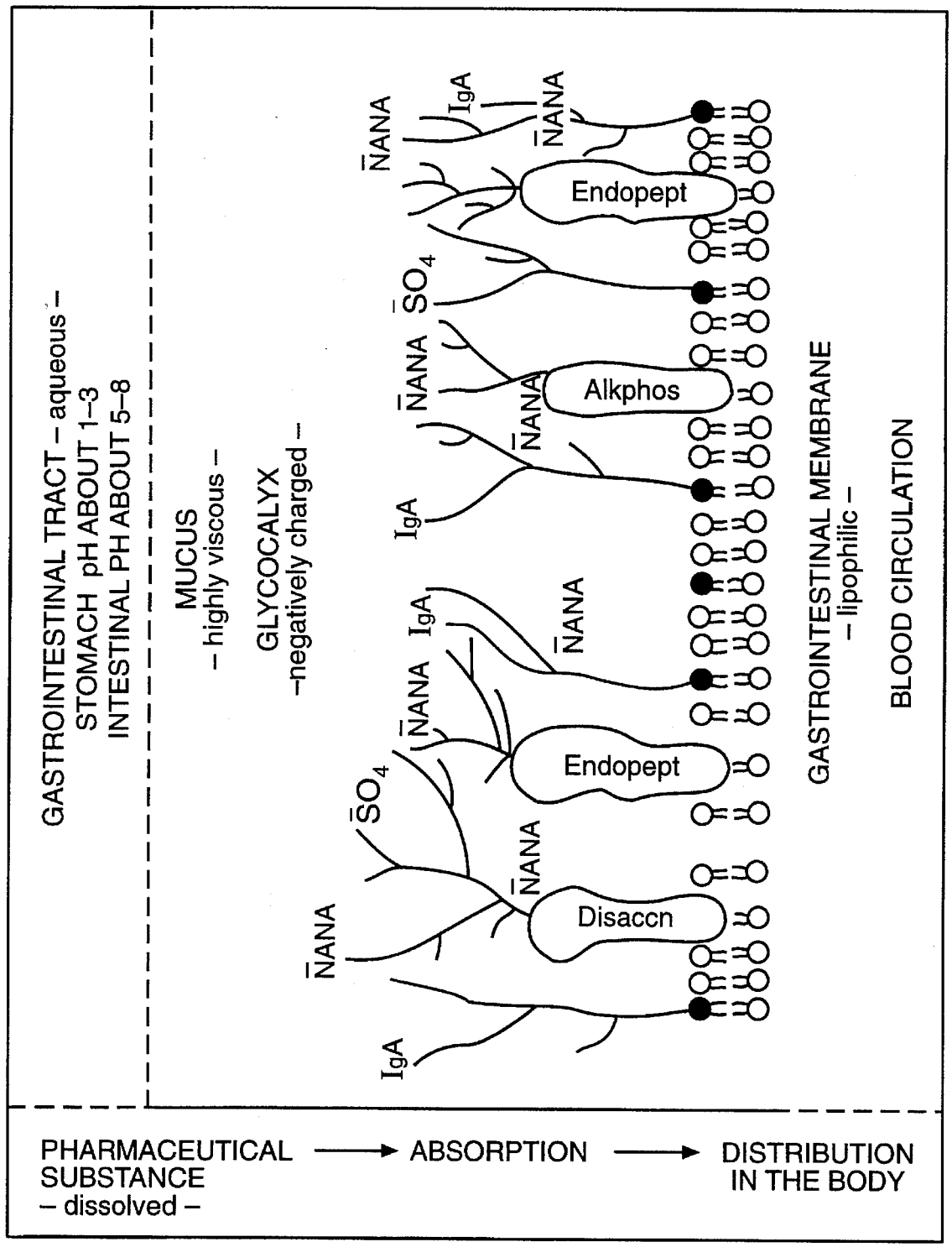
FIG._2

MEDICAMENT CONTAINING A 2-ARYLPROPIONIC ACID DERIVATIVE IN NANOSOL FORM AND ITS PREPARATION

This application is 371 of PCT/DE 92/01012 Dec. 4, 1992.

The invention relates to an immediate-effect medicament for the treatment of painful and/or inflammatory, and also febrile, disorders which as active compound contains a 2-arylpropionic acid derivative in the form of a pharmaceutically administrable nanosol and as excipient essentially contains gelatin, a collagen hydrolyzate or a gelatin derivative in addition to customary pharmaceutical auxiliaries.

The invention furthermore relates to the use of a pharmaceutically administrable nanosol of a 2-arylpropionic acid derivative for the preparation of medicaments having immediate analgesic and/or antirheumatic, and also antipyretic, effect..

The invention finally relates to a process for the preparation of a colloidally disperse system of a 2-arylpropionic acid derivative.

Nonsteroidal antirheumatics (NSAR), such as, for example, the active compounds from the substance class of the salicylic acid derivatives (acetylsalicylic acid), indolylacetic acid derivatives (indometacin), phenylacetic acid derivatives (diclofenac) and oxicams (piroxicam) are employed for the symptomatic therapy of disorders of the rheumatic type. These include, inter alia, rheumatoid arthritis, degenerative forms such as arthroses and spondyloses, and also rheumatic polymyalgia. A differentiation is essentially made between two principal effects: on the one hand the analgesic and antipyretic effect and on the other hand the pronounced antirheumatic/anti-inflammatory effect, which are both based on inhibition of prostaglandin synthesis. With such a therapy, the quality of life of the patients, first and foremost the freedom from pain and the conservation of or improvement in the mobility as well as the chronic progressive course of the disease are favorably affected.

Recently, the pharmacologically active NSAR from the 2-arylpropionic acid derivatives group have gained increasing importance as modern painkillers and antirheumatic agent. Thus in 1987 the painkiller ibuprofen 2-(4-isobutylphenyl)propionic acid or α-methyl-(2-methylpropyl)phenlacetic acid, $C_{13}H_{18}O_2$ already had a 13% share in the total world analgesics market in the non-prescription area alone. Furthermore, the consumption of ibuprofen-containing medicaments rose distinctly in Germany after release from prescription status and ibuprofen is today already described as the painkiller of the 90s.

In addition to ibuprofen, in the coming years the analgesic and antirheumatic structurally related compounds which all possess an asymmetric carbon atom, such as e.g. flurbiprofen, 2-(2-fluoro-4-biphenylyl)propionic acid $C_{15}H_{13}FO_2$, whose racemate is already given in anti-rheumatic therapy at a distinctly lower dose (recommended daily dose 150–200 mg) than racemic ibuprofen (up to 2400 mg daily), ketoprofen, 2- (3-benzoylphenyl)propionic acid $C_{16}H_{14}O_3$, and tiaprofen acid, 2-(5-benzoyl-2-thienyl)propionic acid $C_{14}H_{12}O_3S$, will become the focus of interest. S-Naproxen, (S)-2-(6-methoxy-2-naphthyl)propionic acid $C_{14}H_{14}O_2$, is today already successfully employed in therapy as an enantiomerically pure active compound from this class of substance.

A difficult problem of this active compound group for the pharmacist is to be seen in their poor solubility, because according to the theory of passive transport active compounds are only absorbed in dissolved and undissociated form. In general, by comminuting the active compound (micronizing) it is attempted according to the Noyes-Whitney equation to achieve an increase in the effective substance surface area A, which leads to an increase in the rate of solution. This, in turn, results in an improvement in the bioavailability. Micronized powders are therefore preferably employed today for poorly soluble analgesics/antirheumatics which are to be administered orally.

The technique of micronization is energy-consuming and expensive and problems occur with the very fine dusts, such as e.g. the danger of a dust explosion and the danger of dust inhalation by the personnel, which necessitates extensive protective measures. On account of electrostatic charge, the powder itself is difficult to process with respect to flow properties and is usually poorly wettable (aerophilicity). As a result of the high preparation costs, the price for micronized powder is substantially higher than for conventional powders.

As at present, however, no alternatives present themselves, this measure is taken in order to guarantee an adequate rate of solution in the small intestine, the site of absorption of the 2-arylpropionic acid derivatives.

Without exception, the active compounds of this class of substance are weakly lipophilic acids with $pK_a$ values in the range about 3–5. This brings about a further disadvantage, which is that dissolved or solubilized fractions may recrystallize in contact with the acidic gastric fluid. The resulting crystals can cause gastric irritation. As it is to be assumed that at the acidic gastric pH of 1 the solution equilibrium is largely on the side of the undissolved active compound, this fraction of the active compound dose is thus unavailable for absorption in the stomach.

In order to prevent such an "inactivation" of the active compounds in the acidic pH range, tablets containing these active compounds are customarily provided with enteric coatings. Such measures, however, are not without problems. On the one hand, the stability on storage of these coatings must be put in question, such as, for example, the loss of enteric resistance described in many cases even after one year's storage.

This can have a particularly disadvantageous effect in the case of 2-arylpropionic acid derivatives, as owing to the recrystallization processes described above a drastic restriction of the activity and the side effects described must be expected in the case of defective enteric coatings.

On the other hand, it is known today as a result of improved knowledge about gastric physiology and the motor function of the stomach that particles from a size of 2 mm, i.e. also non-disintegrating enteric-coated tablets or sugar-coated tablets, exhibit a longer residence time depending on the state of fullness of the stomach. Gastric residence times of up to 10 hours result. The time of the initial action is thus barely predictable and a specific therapy with such pharmaceutical forms is usually not possible. These pharmaceutical forms must thus be classified as no longer up to date. Strictly speaking such pharmaceutical forms must therefore no longer be described as immediate-effect forms; they already exhibit "slow release".

The problem of the poor solubility of 2-arylpropionic derivatives is furthermore solved in the prior art by converting the substances into readily water-soluble salts. Ibuprofen is, for example, supplied as a water-soluble lysine salt which, in comparison with the free active compound acid, should cause a more rapid and significantly higher blood level maximum $c_{max}$. Commercially available ibuprofen lysinate-containing tablets are not enteric-coated, so that crystallization of the active compound in the acidic gastric medium with all the abovementioned disadvantages cannot be prevented. A more rapid influx of the active compound into the biophase in under an hour is therefore also not to be expected.

Furthermore, Barabas in U.S. Pat. No. 4,704,436 describes the invention of a water-soluble polyvinylpyrrolidone copolymer complex of ibuprofen. As e.g. derivatives of ethylacrylates or methacrylates are employed as copolymer, side effects possibly occurring as a result of such synthetic polymers must be taken into consideration. The complex with ibuprofen is indeed water-soluble, but the ibuprofen must be released again from this complex by a prior equilibrium. This leads in the case described here to such long dissolving times from the complex that it is even described as suitable for delayed release.

In spite of lower gastrointestinal side effects of the class of substance in comparison with other nonsteroidal antirheumatics, 2-arylpropionic acid derivatives have the great disadvantage that absorption only takes place in the small intestine after a time delay.

For a painkiller, in which a rapid action is desired, this results in a late onset of action. In the case of ibuprofen, the pharmacokinetic parameter $t_{max}$ of 1–2 hours means that after this time the blood level maximum is achieved. Studies exist where, in 2 of 8 subjects investigated, therapeutic concentrations are only achieved after more than 4 hours. With knowledge of these facts it is easily understandable that a patient suffering from pain takes a second or third dose even before the onset of action of the first dose, because the desired analgesic effect apparently fails to materialize. The patient is thus exposed to the danger of an overdose. With a full stomach, the residence times are additionally prolonged so that this effect can be increased as a result.

If, in addition to this factor, the problems of the long gastric residence period of enteric-coated tablets is considered, an even greater value can result for $t_{max}$ in the case of 2-arylpropionic acid derivatives and the patient will also more likely be tempted to take a multiple dose.

J. J. Marty et al., Pharm. Acta Helv. 53, 1 (1978) pp. 17–23 describes the preparation of gelatin nanoparticles in which active compounds can also be included. A pH adjustment during the preparation of these gelatin nanoparticles is proposed for desolvation and resolution. Conversion of the medicament to nanoparticles is not disclosed.

The present invention is therefore based on the object of developing products, and processes for their preparation, for the rapid release of 2-arylpropionic acid derivatives, in particular ibuprofen, flurbiprofen, ketoprofen, tiaprofen acid, and also naproxen, which largely avoid the disadvantages mentioned above for the prior art.

This object is achieved according to the invention in that the medicament contains the analgesic and/or antirheumatic, and also antipyretic 2-arylpropionic acid derivative in the form of a pharmaceutically administrable nanosol and, as excipient, essentially gelatin, a collagen hydrolyzate or a gelatin derivative in addition to customary pharmaceutical auxiliaries. Such a nanosol has an inner phase of the 2-arylpropionic acid derivative which has a particle size of 10–800 nm, preferably of below 400 nm, and possesses a surface charge, an outer phase of gelatin, collagen hydrolyzate or a gelatin derivative which is oppositely charged, and an approximately or completely isoionic charge state of the inner and outer phase.

This object is furthermore achieved by a process for the preparation of a colloidally disperse system of a 2-arylpropionic acid derivative, which comprises selecting a gelatin according to its isoelectric point (IEP) such that its IEP is coordinated with the state of charge of the particles of the 2-arylpropionic acid derivative such that the gelatin leads to charge neutrality at a specific pH with the undissolved particles of the 2-arylpropionic acid derivative; converting the gelatin into the aqueous sol form; adjusting the pH as a function of the IEP of the gelatin to a value such that the nanoparticles of the 2-arylpropionic acid derivative formed are nearly or completely stabilized in neutrally charged form; and before or after the last-mentioned stage dissolving the 2-arylpropionic acid derivative in the aqueous gelatin sol or combining a solution of the 2-arylpropionic acid derivative with the aqueous gelatin sol.

The object in the above sense can also be achieved using fractionated gelatin.

The 2-arylpropionic acid derivative can be present as a racemate, as a racemic mixture, as a pseudo-racemate (mixture of equal amounts of S- and R-enantiomers) or mixtures of different amounts of S- and R-enantiomers in the range between pure S- and pure R-enantiomer.

Embodiments of the medicaments according to the invention, and also of the process for their preparation are mentioned and claimed in the dependent claims.

In the International (PCT) Patent Application of the present date having the title "Pharmazeutisch applizierbares Nanosol und Verfahren zu seiner Herstellung" (Pharmaceutically administrable nanosol and process for its preparation) of ALFATECH-Pharma GmbH corresponding to the German Patent Application P 41 40 195.6 of 5.12.1991, whose contents are also made the contents of the present patent application, nanosols and processes for their preparation are described which make it possible to stabilize colloidally disperse solutions of poorly water-soluble active substances by gelatin, collagen hydrolyzates or gelatin derivatives if the isoionic point (=charge equilibrium) between gelatin and the surface-charged active compound particles is at least approximately established, in this process, the system active compound particle/gelatin is brought to charge equilibrium by compensating the surface charge of the particles by a corresponding opposite charge of the gelatin molecules. This is achieved by establishment of a specific charge on the gelatin molecules which depends on their isoelectric point and the pH of the solution.

FIG. 1 shows a schematic representation of the adjustable states of charge of gelatins as a function of the pH and IEP, it being possible for the IEP to be between 3.5 and 9.5, depending on the manner of preparation. Below pH 3.5, nearly all types of gelatin are positively charged. In the basic range above pH 9.5, all types of gelatin are negatively charged.

FIG. 2 shows the mechanism of passive pharmaceutical substance absorption in the gastrointestinal tract.

According to the invention the fact is therefore utilized that gelatins, collagen hydrolyzates or gelatin derivatives (nearly independently of the viscosity) lead to a stable colloidally disperse system in nanosol form when the isoionic charge state is present between pharmaceutical substance particles and gelatin, collagen hydrolyzate or gelatin derivative.

On the other hand, gelatin according to the prior art was only employed for the stabilization of an inorganic, colloidally disperse system. Thus German Pharmacopoeia 9 describes a colloidal injection solution of radioactive gold which is prepared with gelatin. It was merely proposed here that the macromolecule be present as a "cementing substance" between the individual colloid particles and thus particle aggregation be prevented. However, nothing was known until now about the stabilization mechanism, e.g. for pharmaceutical substances.

The International (PCT) Patent Applications of the present date of ALFATEC-Pharma GmbH and PAZ Arzneimittelentwicklungsgesellschaft mbH corresponding to said German Patent Application (of 5.12.1991) relate to the immediate-effect form of S- and R-ibuprofen (P 41 40 179.4), the sustained-release form of S- and R-ibuprofen (P 41 40 172.7), the immediate-effect form of S- and R-flurbiprofen (P 41 40 184.0) and the sustained-release form of S- and R-flurbiprofen (P 41 40 183.2). Their disclosure is also made the subject of the present patent application.

The advantages of this novel product are thus obvious. As a result of controlled absorption of the active compounds even in the stomach, the rate of influx and bioavailability of 2-arylpropionic acid derivatives which was previously classified as problematical on account of its poor solubility, can surprisingly be significantly improved.

In order to explain the physiological background of the absorption of pharmaceutical substances in general and the improved absorption ratio of the nanosols according to the invention adequately, first a consideration of the mechanism of physiological absorption of pharmaceutical substances as is also presented in relevant publications is necessary. However, the present invention is neither tied to the following attempt of a scientific explanation of the phenomena occurring according to the invention nor can it be restricted by this.

Passive pharmaceutical substance absorption takes place according to the modern state of knowledge (theory according to Brodie et al.), if the following conditions exist:

a) the gastrointestinal membrane acts as a lipid barrier, b) the pharmaceutical substance is only absorbed in dissolved and uncharged, i.e. nonionized, form, c) acidic pharmaceutical substances are preferably absorbed in the stomach and basic pharmaceutical substances preferably in the intestine.

After the oral uptake of a pharmaceutical substance into the body, its absorption, i.e. the crossing into the general circulation (biophase) is prevented to a great degree by physical barriers (see FIG. 2), namely by the mucus layer and an aqueous layer adhering thereto the cell membranes of the intestinal epithelial cells with the glycocalyx covalently bonded thereto and the so-called "tight junctions" which connect the epithelial cells with one another on their apical sides.

These barriers presuppose that absorption of pharmaceutical substances takes place through the lipid double layers fundamentally independently of their distribution mechanism and state of charge (so-called passive diffusion).

The epithelial cells of the entire gastrointestinal tract are covered with a mucus layer which consists of mucins (glycoproteins), electrolytes, proteins and nucleic acids. In particular, the glycoproteins form with the main component of mucus, namely water, a viscous gel structure which primarily performs protective functions for the underlying epithelial layer. The mucus layer is bound to the apical surface of the epithelial cells via the glycocalyx. The glycocalyx likewise has a glycoprotein structure which is covalently bonded to components of the membrane double layer of the epithelial cells. The branched polysaccharides of the glycocalyx, which are either directly covalently bonded to amphiphilic molecules of the double membrane or to the proteins incorporated in the double membrane, possess charged N-acetylneuraminic acid and sulfate radicals and are therefore negatively charged, which can lead to an electrostatic bond or repulsion of charged pharmaceutical substance molecules or of electrostatically charged particles respectively. The epithelial cell membranes consist of phospholipid double layers in which proteins are anchored via their hydrophobie regions. The phospholipid double layers with their lipophilic content represent a further barrier for the transport of the pharmaceutical substances to be absorbed.

From this description, it clearly follows that charged pharmaceutical substance molecules or electrostatically charged particles therefore only have a very low chance of being absorbed via the oral administration route.

The nanosols according to the invention for the first time provide the technical teaching to form a system with which these abovementioned obstacles to absorption can be overcome. As the active compound nanoparticles are stabilized in neutrally charged formby the gelatin according to the invention, they can be transported through the negatively charged glycocalyx without relatively great obstructions, in contrast to other described nanoparticles of the prior art, which are not or cannot be stabilized in neutrally charged form. According to the invention, the adjustment of the isoionic state of charge can additionally be effected in coordination with the physiological conditions (see in particular the explanations on p. 9, lines 14–20 in combination with Examples 1 and 2).

As the active compound nanosols according to the invention can pass through the glycocalyx without obstacle, without being bonded or repelled by electrostatic effects, they thus also reach the surface of the epithelial cells and are available there in a high concentration.

Active, carrier-mediated transport mechanisms or phagocytosis can now also make a significant contribution to the absorption of the active compound nanosols.

Fundamentally, all grades of gelatin are suitable for the preparation of an immediate-effect form if, after processing to give the pharmaceutical form, they are not restricted in their dissolution behavior. For example, spray- or freeze-dried nanosol powders dissolve completely above 37° C. in a few minutes.

If the future pharmaceutical form is a tablet, rapid release times can be achieved, if appropriate with the addition of suitable auxiliaries, by selection of types of gelatin in the molecular weight range below $10^5$ D, preferably in the range $10^4$–$9.5 \times 10^4$ D. Types of gelatin with peptide contents >80% can be directly compressed in a technologically advantageous manner.

Depending on the gelatin preparation procedure (extent of breakdown of native collagen and acidic or alkaline decomposition process), gelatin of Type A or Type B has a characteristic molecular weight spectrum or molecular weight distribution. Table 1 indicates the molecular weight distributions of various types of gelatin or of collagen hydrolyzates, and the percentage content (frequency) of individual molecular weight ranges.

TABLE 1

Molecular weight distribution of various known types of gelatin or of known collagen hydrolyzates

| Molecular Mass Distribution (kD) | Native Collagen % | Gelatin Type B % | Gelatin Type A % | Collagen hydrolyzate Gelita ® Collagel A | Collagen hydrolyzate Gelita ® Collagel B | Collagen hydrolyzate Gelita ® Sol C | Elastin hydrolyzate Gelita ® Gelastin |
|---|---|---|---|---|---|---|---|
| >360 | 100 | 18.0 | 18.0 | 0 | 0 | 0 | 0 |
| 285 | 0 | 7.0 | 9.0 | 0 | 0 | 0 | 0 |
| 145–237 | 0 | 20.0 | 34.0 | 1.0 | 1.5 | 0 | 0 |
| 95 | 0 | 26.0 | 11.0 | 0 | 0 | 0 | 0 |
| 95–50 | 0 | 16.3 | 13.4 | 2.6 | 4.0 | 1.1 | 0 |
| 50–20 | 0 | 7.4 | 9.1 | 18.0 | 14.5 | 0.3 | 0 |
| 20–10 | 0 | 3.9 | 3.8 | 43.0 | 31.6 | 3.7 | 0.2 |
| 10–5 | 0 | 3.0 | 3.0 | 15.4 | 20.0 | 12.2 | 5.2 |
| 5–2 | 0 | 0 | 0 | 6.0 | 14.0 | 26.0 | 93.9 |
| 2–1 | 0 | 0 | 0 | 7.0 | 8.0 | 23.0 | 0 |
| <1 | 0 | 0 | 0 | 6.5 | 7.0 | 34.0 | 0 |
| MW | 360 | 165 | 185 | 12–18 | 12–18 | 3 | 2–3 |

The predominance of an individual range compared with the other molecular weight ranges of the same gelatin can be seen clearly in the individual columns. This range is thus the maximum of the molecular weight distribution (it is 95 kD e.g. for the Type B gelatin shown in the figure). The concept of the "maximum of the molecular weight distribution", however, is to be separated strictly from the concept of the "average mean molecular weight". This mean value is 165 kD for the gelatin of the Type B mentioned.

The nanosols according to the invention exhibit no particle growth in vitro at pH 1–4 within 20 hours or more, i.e. no flocculation or crystallization takes place. This means that the nanosol is available to the gastric mucosa for adequately long during the gastric residence time and independently of pH changes which occur, e.g. as a result of the effect of food, and moreover even independently of the state of fullness of the stomach.

According to the invention, nanosols of the 2-arylpropionic acid derivatives can also be produced which, with respect to their isoionic state of charge, are directly suited to the physiological conditions. Thus, as follows from Example 2, the stability maximum in the acidic range can be increased under the same preparation conditions as in Example 1 solely by appropriate choice of the IEP of the gelatin employed.

After their preparation, the particles of the nanosols are present in nearly monodisperse form in particle sizes of 10 to 800 nm and preferably below 400 nm after resuspension of the dried powder and after resuspension from a pharmaceutical form.

In combination with a rapidly releasing immediate-effect pharmaceutical form as a nanodispersion, the nanosol is well distributed in the stomach, which provides optimum conditions for absorption. Surprisingly, the nanoparticles of the 2-arylpropionic acid derivatives are present in stabilized form even under physiological conditions and as such can be particularly rapidly absorbed without them previously having to be dissolved. Prior solution equilibria, such as are generally known and described in the prior art, are thus inapplicable in any case. They accordingly behave in pharmaceutical use almost as true solutions, but without being one of these.

For the first time, controlled absorption in the gastrointestinal tract is possible even during the gastric residence time as a result of the present invention. The absorption is no longer restricted to the small intestine region in a pH-dependent manner and a rapid influx of 2-arylpropionic acid derivatives is achieved with a correspondingly rapid onset of action.

It is thus possible to achieve for the first time a $t_{max}$ value of less than 2 h, in particular less than 1 h, with these pharmaceutical substances.

Surprisingly, an increase in the blood level maximum value $c_{max}$ can also be determined. The increase in $c_{max}$ can therefore in certain circumstances result in a dose reduction with the same activity.

In addition to the rapid onset of action, the rapid influx leads to an earlier elimination from the plasma so that the systemic loading is reduced compared with conventional medicaments. The duration of action itself is in practice not reduced by this, because at the site of action, in particular in inflammatory processes, a substantially longer residence period of the active compound can be expected. The half-lives in the plasma in the case of ibuprofen are, for example, about 2 h. In the synovial fluid, on the other hand, half-lives of 10 h to 12 h were found.

As in vitro experiments have shown, as a result of the long stabilities of the nanosols according to the invention no recystallization can take place in the stomach.

Herein lies a further substantial advantage of the present invention: it is known that especially in older patients with the most frequent incidence of rheumatic disorders the severity of the active compound-related side effects also increases. This applies to a particular extent for the long-term therapy of the chronically ill. As in a 2-arylpropionic acid derivative nanosol the active compound is then virtually present "embedded" in gelatin and cannot be recrystallized as it is not present in dissolved form, protection of the mucous membrane in the gastrointestinal tract is also to be expected due to the nontoxic biopolymer gelatin.

In the formulation of immediate-effect or sustained-release preparations, the pharmacist makes a fundamental difference between:

1. pharmaceutical preparation, i.e. of the release of the pharmaceutical substance, e.g. from a tablet in a manner which is rapid (immediate-effect form) or prolonged (sustained-release form) timewise;

and 2. the pharmaceutical substance-specific absorption site, such as e.g. the stomach or specific sections of the intestine.

The nanosols according to the invention are able, independently of the pharmaceutical preparation, to be absorbed in the entire gastrointestinal region on account of their special composition. They can therefore be advantageously processed to give immediate-effect or sustained-release pharmaceutical forms.

The immediate-effect nanosols claimed in the context of this invention can be combined with sustained-release nanosols in a novel manner. If, for example, high molecular weight types of gelatin are employed, nanosols having a sustained-release action can be obtained. A particular embodiment which is suitable for these sustained-release nanosols is e.g. a matrix tablet, as is described in the International (PCT) Patent Application having the title "Sol-gesteuerte Thermokolloidmatrix auf Gelatinebasis für perorale Retardformen" (Sol-controlled thermocolloid matrix based on gelatin for oral sustained-release forms) (11 AL2713) of ALFATEC-Pharma GmbH of the same date, which corresponds to the German Patent Application P 41 40 192.1. Its disclosure is also made a subject of the present patent application.

Useful combinations may be e.g.: immediate-effect S-ibuprofen with sustained-release S-ibuprofen, immediate-effect R-flurbiprofen (analgesic) with sustained-release S-flurbiprofen (anti-inflammatory) and others.

The dried nanosol can be processed to give pharmaceutical forms, for example to give a tablet, and resuspended from this. An enteric coating for protection from "inactivation" of the active compound by the acidic stomach pH is thus superfluous.

The risk of an overdose due to taking repeatedly is excluded by the rapid onset of the analgesia as a result of absorption in the stomach. All the disadvantages and dangers of the enteric coating mentioned are inapplicable. The present invention thus also serves to increase patient compliance. This all constitutes a decisive contribution to the medicament safety demanded.

Fundamentally, the product according to the invention can be processed to give all pharmaceutical forms which are to be administered orally, in particular it can be filled into hard gelatin capsules directly as a powder. It is also outstandingly suitable for direct tableting. Processing to give beverage granules, rapidly dissolving pellets or beverage tablets is of particular interest for administration as an immediate-effect form which has a rapid influx.

In addition, the nanosols according to the invention can also be employed for processing into ointment, cream or gel bases for the topical application field (rheumatic ointments).

In principle, the procedures and process variants mentioned in the abovementioned German Patent Application P 41 40 195.6 of ALFATEC-Pharma GmbH "Pharmazeutisch applizierbares Nanosol und Verfahren zu seiner Herstellung" (Pharmaceutically administrable nanosol and process for its preparation), which are referred to once more in the following, are suitable for the preparation of the nanosols according to the invention:

Several processes for the preparation of the nanosols are proposed. These are an exemplary, incomplete list. The person skilled in the art can independently work out further variants in the context of the present invention on the basis of his expert knowledge:

Process I

This can be used if the pharmaceutical substance is soluble in a mixtures of: a water-miscible organic solvent and water, or several water-miscible organic solvents and water:

a) a gelatin selected in the preliminary tests is converted into sol form with water;

b) the pH of the solution found in the preliminary tests is adjusted; c) one or more water-miscible, organic solvent(s), preferably ethanol, isopropanol or methanol, is/are added to this solutions d) the pharmaceutical substance is added to the solution in solid form and dissolved;

e) the organic solvent (s) is/are removed, preferably by evaporating in vacuo; the nanosol is formed during the course of this;

f) the colloidally disperse solution is then dried, preferably by spray- or freeze-drying.

The organic solvent has the aim of dissolving the pharmaceutical substance and also changes the hydration shell of the gelatin molecules.

Process II

This embodiment can be used if the pharmaceutical substance is an acid or a base whose salt is soluble in water:

a) a gelatin selected in the preliminary tests is converted into the sol form with $H_2O$;

b) a pH is set which enables formation of the salt of the pharmaceutical substance;

c) the pharmaceutical substance is dissolved in the gelatin sol with salt formation;

d) by addition of alcohol or similar organic solvents, the hydration shell of the gelatin molecules can be loosened;

e) by addition of a suitable amount of acid or base the pH is set which leads to the formation of the isoionic point (IIP) and the nanosol results;

f) the colloidally disperse solution is dried as in process I. Stage d) is optional, but preferred.

Process III

This embodiment can be used if the pharmaceutical substance is a neutral substance:

a) a gelatin sol is prepared as described in (1) a) and b).

b) a second solution is prepared from a water-miscible organic solvent, preferably ethanol, methanol, isopropanol or acetone and the pharmaceutical substance.

c) the two solutions are combined.

d) the organic solvent is removed and the colloidally disperse solution is dried.

Process IV a) As described in (I) a) and b).

b) A colloidally disperse system is briefly formed with the pharmaceutical substance, but without gelatin, in a second solution.

c) The solution obtained in (b) is continuously combined with the gelatin solution.

In step (IV) c) the continuous mixing of the solutions described in (IV) a) and b) can be controlled in a time-dependent manner by on-line measurement of the particle size using a suitable process, such as e.g. by laser light scattering (BI-FOQELS On-line Particle Sizer). It is thus possible to continuously set a desired particle size.

All processes mentioned are also suitable for collagen hydrolyzates and gelatin derivatives and can be applied without problems on the industrial scale.

The essential steps can largely run in an automated manner, it also being possible to carry out processes I to III continuously. In the case of the immediate-effect form for 2-arylpropionic acid derivatives, variant Nos. II and III may be mentioned as preferred processes.

All gelatins, gelatin derivatives, collagen hydrolyzates and fractionated gelatins, and also their mixtures are suitable for the immediate-effect forms according to the invention. Types of gelatin which have an isoelectric point (IEP) described according to the invention which is not commercially available can be prepared according to Examples I to III from the abovementioned German Patent Application.

Compared with commercially available products, the use of gelatin which has been prepared in a special manner leads to nanosols described according to the invention having increased stability.

Examples of the preparation of grades of gelatin particularly suitable according to the invention are given below.

Examples of the preparation of particularly suitable types of gelatin according to the invention with isoelectric points of 3.5 to 9.5

EXAMPLE I

Process for obtaining an IEP of 7.5 to 9.5

Collagen-containing starting material such as e.g. pig skins are treated for 12 to 20 hours with an aqueous solution of a 0.45N mineral acid, preferably sulfuric acid, in a liquor ratio of 1:1. The excess of acid is then removed by washing several times, it being possible to use sodium hydrogen carbonate to shorten the process. The extraction of the stock-rich material is carried out using hot water at 55°–80° C. at a pH of 2.5 to 4.5. At pHs below 3.5 an IEP of 8.5 to 9.5 can be achieved, at pHs above 3.5 the IEP is 7 to 8.5. In this manner, various IEPs from 7 to 9.5 can be achieved as a direct function of the pH during the extraction.

After the extraction process step, the aqueous solution is neutralized and worked up as customary.

Depending on the temperature selected during the extraction, types of gelatin having high to medium molecular weight distributions can furthermore be obtained by this process.

At temperatures of 50°–55° C., particularly highly viscous and high-bloom grades are obtained. Types of gelatin having low molecular weight or cold water-soluble gelatins can be obtained by controlled degradation with collagenases.

EXAMPLE II

Process for achieving an IEP of 4 to 7.5

The collagen-containing starting material is first washed to remove foreign substances and comminuted, and then homogeneously rendered alkaline by addition of magnesite, sodium hydroxide solution or calcium hydroxide by thorough mixing in the liquor ratio 1:1.2. The material pretreated in this way is briefly hydrolyzed by pressure hydrolysis at $1.01\times10^5$ to $2.02\times10^5$ Pa and a pH of the aqueous solution of 8–14. After hydrolysis, it is immediately neutralized and the still hot aqueous gelatin solution is filtered, deionized, concentrated and dried in the usual manner.

If a weakly basic hydrolyzing agent such as magnesite is taken, an IEP of 6 to 7.5 is obtained if the reaction is carried out at $1.01\times10^5$ Pa. IEPs of 5 to 6 are obtained when using a dilute milk of lime suspension and when using 0.005 to 0.1N sodium hydroxide solution IEPs of 4 to 5 can be achieved.

Types of gelatin having a low degree of racemization and a low peptide content can be obtained with pressure ratios of $1.01\times10^5$ Pa and residence times of at most 10 min.

Medium to low molecular weight types to cold water-soluble types are afforded by correspondingly longer residence times.

EXAMPLE III

Process for achieving an IEP of 3.5 to 6

Collagen-containing starting material, preferably split or ossein is subjected after the starting wash to treatment with a high-speed asher. In this case, two process variants in the liquor ratio 1:1.3 offer themselves, which either use a saturated milk of lime suspension or a 0.1 to 1N sodium hydroxide solution.

When using a milk of lime suspension, the raw material is hydrolyzed for a maximum of 3 to 4 weeks with continuous agitation. The material is then neutralized by addition of acid and washed several times. Further working up follows in the usual manner. IEPs of 4 to 6 can be obtained in this manner.

When using sodium hydroxide solution, the asher process can be shortened again, the material, depending on the degree of comminution, being hydrolyzed even after 6–12 hours at concentrations of 1N sodium hydroxide solution. Neutralization is carried out using equimolar amounts of mineral acid and the neutral salts are removed by washing several times or by deionizing the aqueous gelatin solution obtained in the extraction. In this process variant, IEPs of 3.5 to 5 can be obtained.

Particularly low-peptide types of gelatin are obtained with a short residence time in the asher. Types of gelatin with high to average molecular weight distribution ($M=10^4$–$10^7$ D) can thus be obtained.

Low molecular weight to cold water-soluble types of gelatin can be obtained by thermal degradation or enzymatically.

In the case of the 2-arylpropionic acid derivatives, types of gelatin having an IEP of 3.5 to 9.5 are preferably employed.

Customary pharmaceutical auxiliaries and/or other macromolecules, if they are technologically necessary, can be added to the nanosols according to the invention in the liquid or dry state.

For example, an addition of polyvinylpyrrolidone in the quantitative ratio gelatin to polyvinylpyrrolidone in the range from 5:1 to 500:1 may be suitable.

The technological processing properties of an immediate-effect form within the meaning of the invention, which is processed e.g. to give tablets or is to be lyophilized, can be improved by addition of low molecular weight types of polyvinylpyrrolidone in the range from 10:1 to 50:1 without the stability of the nanosols being adversely affected.

The preferred preparation processes, procedures and names in the following examples relate as follows to the German Patent Application "Pharmazeutisch applizierbares Nanosol und Verfahren zu seiner Herstellung" (Pharmaceutically administrable nanosol and process for its preparation) (P 41 40 195.6) or the abovementioned processes and examples:

Nanosol preparation: Processes II and III

Gelatin preparation: Examples I to III

Preliminary test: see the following description:

Preliminary test:

As already mentioned at the beginning and as is evident from FIG. 1, the absolute, maximum possible net charge of an individual gelatin molecule depends mainly on the number of free COOH and $NH_2$ groups and the pH of the solution. As Type A, B, collagen hydrolyzates or gelatin derivatives differ in the number of free COOH groups, their maximum possible net charge is thus also different. With gelatin derivatives, the state of charge can additionally depend on the type of modification.

When carrying out the process according to the invention, the suitable gelatin and the suitable pH are selected in a preliminary test.

First, a working pH range suited to the physicochemical properties of the pharmaceutical substance is selected. Physicochemical properties of the pharmaceutical substance to be taken into account in particular are: the solubility (in organic solvents or water), its properties as an acid, base or neutral substance and its stability to acids and alkali solutions.

In a first rapid test it is determined what charge the precipitated particles have. This results, taking into account the working pH range, in the choice of a suitable type of gelatin. If the particles are, for example, negatively charged, a gelatin is picked which is positively charged under the given pH conditions. This rapid test for the determination of the particle charge has the advantages that it can be carried out without a great outlay in terms of apparatus and time. A time-consuming and inaccurate zeta potential measurement can thus be dispensed with entirely.

In many cases, it will be adequate for this rapid test to convert two commercially available Type A and B gelatins with an IEP of 9.5 or 3.5 respectively and with peptide contents of <30% and a bloom number of 200, which are additionally designated as standard gelatins, into the sol form at a pH of 6 (5% strength aqueous solution) and to dissolve the pharmaceutical substance in a water-miscible solvent, such as e.g. ethanol, isopropanol or acetone, and in each case to mix homogeneously with the gelatin solutions. At the same dose of the pharmaceutical substance, in the case of the gelatin which is unsuitable in its state of charge a colloidal system will either not form or immediately become unstable or the pharmaceutical substance will flocculate. If the resulting particles are negatively charged, they are stabilized rather by the gelatin solution of Type A, which is positively charged at a pH of 6, than by the solution containing Type B gelatin; in contrast, in this case Type B either will form no colloidal system or the system will immediately destabilize. The flocculation of the particles can be monitored e.g. via a simple turbidity measurement.

In this rapid test, the working pH range must be taken into account in each case. Other gelatins can also be selected as standards, but they must be selected in their IEP such that they carry an opposite net charge at this pH (see also FIG. 1). In most cases, said standard Type A and B gelatins are adequate for this rapid test.

Starting from the result of the preliminary experiment, the optimum conditions for the formation of the nanosols are determined by stepwise variation of the IEP by use of appropriate types of gelatin and of the pH of the solution in relatively small ranges (e.g. 0.1 pH steps), i.e. the stability optimum which is characterized by the isoionic point (IIP) must be found in order to guarantee an adequate stability for the pharmaceutical applications mentioned.

It can be the case that a stability of the nanosols which is acceptable within the meaning of the invention is already found in a relatively narrow pH range (about 0.5 units) around the isoionic point, so that an adjustment of this point itself is not absolutely necessary. On the other hand, several gelatins can also lead to the same, stable results. Thus, for example (Example 5) with the oral antidiabetic glibenclamide in the case of a Type B gelatin with an IEP of 5.5, the stability optimum can be at a pH of 3.2, while in the case of a Type B gelatin with an IEP of 3.8 the stability optimum is at a pH of 2.2.

Characterized by a stability maximum, in both cases the isoionic point was reached (the dependence of the net charge on the pH and the IEP must be non-linear, as it is given by the $pK_a$ value of the COOH or $NH_3^+$ groups present).

The following examples are intended to illustrate the invention in greater detail:

EXAMPLE 1

Pharmaceutical substance:
  Ibuprofen (racemate), active compound acid
Gelatin type:
  Commercially available, Type B, 40 bloom
Nanosol preparation:
  Analogously to Process II
Weight ratio gelatin/pharmaceutical substance: 2:1
  The working pH range for ibuprofen is below its $pK_a$ of 4.6
  At a pH of 3.0, a type B gelatin (IEP 4.9) has a stability maximum.
  10 kg of a 6% strength aqueous gelatin solution are prepared using distilled water (40° C.).
  300 g of racemic ibuprofen are dissolved with stirring in 800 g of sodium hydroxide solution (10%) and combined with the gelatin solution. The mixture is stirred at 40° C. until a completely clear solution is formed. It is then adjusted to pH 3.0 by addition of hydrochloric acid, whereupon the nanosol forms.
  After concentration and spray-drying, tablets in each case having a content of ibuprofen of 200 mg are prepared from the powder obtained with the addition of customary auxiliaries.
  Under in vitro conditions (900 ml of artificial gastric juice/pH 1, 37° C.), particle growth (BI-FOQUELS On-line Particle Sizer) commences within 13 hours.

EXAMPLE 2

A nanosol is produced as in Example 1, but a gelatin having an IEP of 3.6 is selected which has a stability optimum at a pH of 2.

Under the same test conditions (Example 1), particle growth of the nanosol obtained commences after 15 hours on average.

EXAMPLE 3

Pharmaceutical substance:
  R-flurbiprofen, enantiomerically pure active compound acid
Gelatin type:
  Type B, 120 bloom, preparation Example II
Nanosol preparation:
  Analogously to process III
Weight ratio gelatin/pharmaceutical substance: 5:1
  The working pH range for R-flurbiprofen is below its $pK_a$ value of 4.16.
  At a pH of 3.2, the preliminary test according to the invention and the series of measurements shows an optimum with a type B gelatin (IEP 4.5) for the isoionic charge state.

10 kg of a 6% strength aqueous gelatin solution are prepared at 40° C. using distilled water and 15 g of PVP K 15 are dissolved therein. The mixture is adjusted to pH 3.2 by addition of hydrochloric acid (15% strength).

120 g of R-flurbiprofen are dissolved in 700 ml of isopropanol. Both solutions are homogeneously mixed and the organic solvent is removed in vacuo.

The resulting nanosol is spray-dried and pressed in the customary manner to give tablets with a content of R-flurbiprofen of 50 mg.

In the dissolution test according to USP XXII (900 ml of water, paddle, 65 rpm, 37° C.), the tablets show complete dissolution within 15 minutes.

EXAMPLE 4

A tablet which is produced under identical conditions to those in Example 3 but contains no addition of PVP K 15 shows complete dissolution under identical test conditions within 25 minutes.

EXAMPLE 5

Pharmaceutical substance:
  R-flurbiprofen, enantiomerically pure active compound acid
Gelatin type:
  Commercially available, type B, 190 bloom
Nanosol preparation:
  Analogously to process III
Weight ratio gelatin/pharmaceutical substance: 1.5:1

The preparation conditions of the nanosol correspond to Example 3, using an identically charged gelatin which, however, has a higher bloom value. The quantitative ratios are as follows:
Gelatin:
  150 g dissolved in 1.5 l of distilled water
R-flurbiprofen:
  100 g dissolved in 500 ml of isopropanol
PVP K 15:
  15 g dissolved at 40° C. in the gelatin solution After removal of the isopropanol by evaporation, the nanosol is lyophilized. The nanosol, which is filled into hard gelatin capsules in each case with a content of R-flurbiprofen of 25 mg dissolves completely in aqueous medium under the test conditions as in Example 3 within 5 minutes.

The capsules thus produced show blood level maximum values which are on average less than one hour.

EXAMPLE 6

Pharmaceutical substance:
  Ketoprofen (racemate), active compound acid
Gelatin type:
  Type A, collagen hydrolyzate, MW<10$^4$ D, preparation Example I
Nanosol preparation:
  Analogously to process II
Weight ratio gelatin/pharmaceutical substance: 6:1

The working pH range for ketoprofen is below the pK$_a$ of 5.3.

The rapid test at pH 4.5 for determination of surface charge of the ketoprofen particles does not yield any nanosol with the standard type B gelatin (IEP 3.5/200 bloom). Under identical test conditions, the standard type A gelatin (IEP 9.5/200 bloom) yields a briefly stable nanosol. A negative surface charge of the ketoprofen particles is thus detectable.

In the following experiments for determination of the optimum collagen hydrolyzate, a type A, which has been completely freed from foreign ions by ion exchangers and has an IEP of 8, at a pH of 3.8 is best suited.

A solution of 300 g of the collagen hydrolyzate described above in 6 l of water is prepared at 20° C. 50 g of ketoprofen are dissolved in 300 g of 10% sodium hydroxide solution and added to the aqueous hydrolyzate solution. After intensive thorough mixing, the clear solution is brought to a pH of 3.8 by addition of a measured amount of acid. The nanosol prepared in this way has to 60% a particle size of less than 410 nm.

After concentration and spray-drying, the nanosol is processed to give tablets in each case with a ketoprofen content of 50 mg (direct tabletting).

Under the test conditions as in Example 3, the tablet dissolves completely within 10 minutes.

EXAMPLE 7

Analogously to Example 6, the powder thus obtained is granulated and individually filled as granules with a dose of 50 mg of ketoprofen. The granules dissolve completely at 20° C. in aqueous medium within 3 minutes.

The granules obtained can also be present as an initial dose in a hard gelatin capsule in combination with a nanosol matrix tablet or conventional sustained-release forms.

We claim:

1. An immediate-effect medicament for the treatment of painful, inflammatory, and febrile disorders, containing a pharmacologically active 2-arylpropionic acid derivative in the form of a pharmaceutically administrable nanosol which, as excipient, comprises gelatin, a collagen hydrolyzate or a gelatin derivative.

2. A medicament as in claim 1, wherein the nanosol
   a) has an inner phase of the 2-arylpropionic acid derivative which has a particle size of 10–800 nm and possesses a surface charge,
   b) an outer phase of gelatin, a collagen hydrolyzate or a gelatin derivative which is oppositely charged,
   c) a nearly or completely isoionic state charge of the inner and outer phase, and
   d) is physiologically absorbable.

3. A medicament as in claim 1, wherein the 2-arylpropionic acid derivative is present as a racemate or as a mixture of the racemate and its enantiomers.

4. A medicament as in claim 1, wherein the 2-arylpropionic acid derivative is present as a pseudoracemate.

5. A medicament as in claim 1, wherein the 2-arylpropionic acid derivative is present as a pure S-enantiomer or as a pure R-enantiomer.

6. A medicament as in claim 1, wherein the 2-arylpropionic acid derivative is present as a mixture of S- and R-enantiomers.

7. A medicament as in claim 1, wherein the 2-arylpropionic acid derivative is present as a liquid, aqueous nanodispersion.

8. A medicament as in claim 1, wherein the 2-arylpropionic acid derivative is present as a solid, resuspendable nanodispersion.

9. A medicament as in claim 1, wherein the 2-arylpropionic acid derivative has an average particle size of below 400 nm.

10. A medicament as in claim 1, comprising an outer phase of the nanosol which additionally contains polyvinylpyrrolidone in a weight ratio of gelatin, collagen hydrolyzate or gelatin derivative to polyvinylpyrrolidone in the range of 5:1 to 500:1.

11. A medicament as in claim 1, wherein the 2-arylpropionic acid derivative is ketoprofen.

12. A medicament as in claim 1, wherein the 2-arylpropionic acid derivative is S-naproxen.

13. A medicament as in claim 10, wherein the weight ratio is in the range of 10:1 to 50:1.

14. A medicament as in claim 1, wherein the excipient is gelatin.

15. A medicament as in claim 14, wherein the gelatin has a maximum in the molecular weight distribution in the range of $10^4$ to $10^7$ D.

16. A medicament as in claim 14, wherein the gelatin has a maximum in the molecular weight distribution of less than $10^5$ D.

17. A medicament as in claim 14, wherein the gelatin has a maximum in the molecular weight distribution in the range of $10^4$ to $9.5 \times 10^4$ D.

18. A medicament as in claim 14, wherein the gelatin has a bloom value between 0 and 50.

19. A medicament as in claim 1, wherein the excipient further comprises a customary pharmaceutical auxiliary.

20. A medicament as in claim 19, wherein the auxiliary is polyvinylpyrrolidone.

21. A medicament as in claim 1, wherein the excipient consists essentially of a gelatin, a collagen hydrolyzate, or a gelatin derivative.

22. A medicament of claim 1, wherein the excipient consists essentially of a gelatin, a collagen hydrolyzate, or a gelatin derivative and a customary pharmaceutical auxiliary.

23. A medicament as in claim 22, wherein the auxiliary is polyvinylpyrrolidone.

24. A medicament as in claim 1, wherein the excipient consists essentially of gelatin.

25. A medicament as in claim 1, wherein the excipient consists essentially of gelatin and a customary pharmaceutical auxiliary.

26. A medicament as in claim 25, wherein the auxiliary is polyvinylpyrrolidone.

* * * * *